(12) United States Patent
Kedl et al.

(10) Patent No.: US 7,427,629 B2
(45) Date of Patent: Sep. 23, 2008

(54) IMMUNOSTIMULATORY COMPOSITIONS AND METHODS OF STIMULATING AN IMMUNE RESPONSE

(75) Inventors: Ross M. Kedl, Roseville, MN (US); George W. Griesgraber, Eagan, MN (US); Isidro Angelo E. Zarraga, Minneapolis, MN (US); Paul D. Wightman, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 467 days.

(21) Appl. No.: 10/640,904

(22) Filed: Aug. 14, 2003

(65) Prior Publication Data

US 2004/0091491 A1    May 13, 2004

Related U.S. Application Data

(60) Provisional application No. 60/403,846, filed on Aug. 15, 2002.

(51) Int. Cl.
*A61K 31/44* (2006.01)
(52) U.S. Cl. .................................................. 514/279
(58) Field of Classification Search ................ None
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gerster | |
| 5,346,905 A | 9/1994 | Gerster | |
| 5,350,836 A * | 9/1994 | Kopchick et al. | 530/399 |
| 5,352,784 A | 10/1994 | Nikolaides et al. | |
| 5,367,076 A | 11/1994 | Gerster | |
| 5,376,501 A | 12/1994 | Mariën et al. | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,521,289 A | 5/1996 | Hainfeld et al. | |
| 5,693,811 A | 12/1997 | Lindstrom | |
| 5,741,908 A | 4/1998 | Gerster et al. | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,338 B1 | 2/2001 | Andolfatto et al. | |
| 6,194,425 B1 | 2/2001 | Gerster et al. | |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,340,461 B1 | 1/2002 | Terman | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,451,810 B1 | 9/2002 | Coleman et al. | |
| 6,476,000 B1 | 11/2002 | Agrawal | |
| 6,518,265 B1 | 2/2003 | Kato et al. | 514/228.5 |
| 6,525,064 B1 | 2/2003 | Dellaria et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,660,747 B2 | 12/2003 | Crooks et al. | |
| 7,030,129 B2 | 4/2006 | Miller et al. | |
| 2002/0022248 A1 * | 2/2002 | Xu et al. | 435/69.1 |
| 2002/0055517 A1 | 5/2002 | Smith | |
| 2002/0058674 A1 | 5/2002 | Hedenstrom et al. | 514/292 |
| 2003/0022302 A1 | 1/2003 | Lewis et al. | |
| 2003/0139364 A1 * | 7/2003 | Krieg et al. | 514/44 |
| 2004/0014779 A1 | 1/2004 | Gorden et al. | |

(Continued)

FOREIGN PATENT DOCUMENTS

EP        0 394 026        10/1990

(Continued)

OTHER PUBLICATIONS

Agrawal, et al. Nature Biotech 22: 1534-1537, 2004 Antisense and siRNA as agonists of Toll-like receptors.*
Bernstein, et al. Vaccine 13: 72-76, 1995 'Effect of imiquimod as an adjuvant for immunotherapy of genital HSV in guinea-pigs'.*
Kirkley, et al. Scand. J. Immunol. 43: 431-438, 1996 'Adjuvant Properties of Montanide CSA 720 with a recombinant HIV P17 gag Protein and synthetic peptide antigens'.*
Du, et al. World J. Gastroenterol. 9(1): 108-111, 2003 'HBV DNA vaccine with adjuvant cytokines induced specific immune response against HBV infection'.*
Aduzzi, a, Prions and the immune system: a journey through gut, spleen, and the nerves, Adv. Immunol., 81:123, 2003 (Abstract only).*

(Continued)

*Primary Examiner*—Prema Mertz
(74) *Attorney, Agent, or Firm*—Ted K. Ringsred

(57)    ABSTRACT

The present invention provides immunostimulatory compositions that include an immune response modifier portion paired with an antigenic portion.

5 Claims, 6 Drawing Sheets

U.S. PATENT DOCUMENTS

| | | | |
|---|---|---|---|
| 2004/0023870 | A1 | 2/2004 | Dedera et al. |
| 2005/0220883 | A1* | 10/2005 | O'Hagan et al. ............ 424/489 |

FOREIGN PATENT DOCUMENTS

| | | |
|---|---|---|
| EP | 1 104 764 | 6/2001 |
| JP | 9-208584 | 8/1997 |
| JP | 11-80156 | 3/1999 |
| JP | 11-222432 | 8/1999 |
| JP | 2000-247884 | 9/2000 |
| WO | WO 00/40228 | 7/2000 |
| WO | WO 00/47719 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/086280 | 10/2003 |
| WO | WO 03/089602 | 10/2003 |

OTHER PUBLICATIONS

Adamsson et al., Novel Immunostimulatory agent based on CpG oligonucleotide linked to the nontoxic B subunit of cholera toxin, J. immunol., 176(8):4902-13, Apr. 15, 2006.*

Muller et al., Specific antibody response towards predicted epitopes of the epidermal growth factor receptor induced by a thermostable synthetic peptide adjuvant conjugate, Clin. Exp. Immunol., 78(3):499-504, Dec. 1989.*

Francklyn, C., Aminoacyl-tRNA Synthetases: Versatile Players in the Changing Theater of Translation, RNA, vol. 8, pp. 1363-1372 (2002).*

Goodman & Gilman's The Pharmacological Basis of Therapeutics, 9th Ed., McGraw-Hill, NY, (1996).*

Nagase, H., et al., The Pharmacological Profile of δ Opioid Receptor Ligands, (+) and (-) TAN-67 on Pain Modulation, Life Sciences, vol. 68, pp. 2227-2231 (2001).*

Kick, E.K., et al., Structure-Based Design and Combinatorial Chemistry Yield Low Nanomolar Inhibitors of Cathepson D, Chemistry & Biology, vol. 4, No. 4, pp. 297-307 (1997).*

Immunobiology, The Immune System in Health and Disease, Third Edition, Janeway, And Travers, Ed., 1997.*

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

Akira S. et al., "Recognition of pathogen-associated molecular patterns by TLR family", *Immunology Letters*, 2003, vol. 85, pp. 85-95.

Ozinsky A. et al., "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Vasllakos et al., *Cellular Immunology*, vol. 204, pp. 64-74 (2000).

Wagner et al., *Cellular Immunology*, vol. 191, pp. 10-19 (1999).

Izumi et al.; "1H-Imidazo[4,5-c]quinoline Derivatives as Novel Potent TNK-α Suppressors: Synthesis and Structure-Activity Relationship of 1-, 2-and 4-Substituted 1H-imidazo[4,5-c]quinolines or 1H-imidazo[4,5-c]pyridines"; Bioorganic & Medicinal Chemistry; 11; (2003) pp. 2541-2550.

Testerman, et al., "Cytokine Induction by the Immunomodulators Imiquimod and S-27609", *Journal of Leukocyte Biology*, vol. 58, pp. 365-372, Sep. 1995.

Chollet, et al, "Development of a Topically Active Imiquimod Formulation", *Pharmaceutical Development and Technology*, 4(1), pp. 35-43 (1999).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002 pp. 196-200.

Medzhitov, "Toll-Like Receptors and Innate Immunity", *Nature Reviews Immunology*, Vo. 1, Nov. 2001, pp. 135-145.

Jurk et al. "Human TLR7 and TLR8 independently confer responsiveness to the antiviral compound R-848", *Nature Immunology*, Jun. 2002, vol. 3, No. 6: p. 1.

Akira et al., "Toll-like receptors: critical proteins linking innate and acquired immunity", *Nature Immunology*, Aug. 2001, vol. 2, No. 8; pp. 675-680.

Shirota et al.; "Regulation of Murine Airway Eosinophilia and Th2 Cells by Antigen-Conjugated CpG Oligodeoxynucleotides as a Novel Antigen-Specific Immunomodulator"; *The Journal of Immunology*; 2000; pp. 5575-5582.

Shirota et al. "B Cells Capturing Antigen Conjugated with CpG Oligodeoxynucleotides Induce Th1 Cells by Elaborating IL-12"; *The Journal of Immunology*; 2002; pp. 787-794.

Brassard et al.; "Interferon-α as an immunotherapeutic protein"; Journal of Leukocyte Biology; vol. 71, Apr. 2002; pp. 565-581.

* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: Murine SIINFEKL Peptide

<400> SEQUENCE: 1

Ser Ile Ile Asn Phe Glu Lys Leu
1               5
```

IMMUNOSTIMULATORY COMPOSITIONS AND METHODS OF STIMULATING AN IMMUNE RESPONSE

CROSS-REFERENCE TO RELATED APPLICATION

This application claims priority to U.S. Provisional Patent Application No. 60/403,846, filed Aug. 15, 2002.

BACKGROUND

Immune response modifiers ("IRMs") include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain TH-2 cytokines, such as IL-4 and IL-5. Additionally, some IRM compounds are said to suppress IL-1 and TNF (U.S. Pat. No. 6,518,265).

Certain IRMs are small organic molecules (e.g., molecular weight less than about 1000 Daltons, in certain cases less than about 500 Daltons, as opposed to large biologic protein, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; and 6,573,273; European Patent 0 394 026; U.S. Patent Publication No. 2002/0055517; and International Patent Publication Nos. WO 01/74343; WO 02/46188; WO 02/46189; WO 02/46190; WO 02/46191; WO 02/46192; WO 02/46193; WO 02/46749 WO 02/102377; WO 03/020889; WO 03/043572 and WO 03/045391.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain benzimidazole derivatives (such as those described in U.S. Pat. No. 6,387,938), and certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08595).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Certain IRMs can function as Toll-like receptor (TLR) agonists. Some small molecule IRMs may act through one or more of TLRs 2, 4, 6, 7, and 8. CpG may act through TLR 9.

By stimulating certain aspects of the immune system, as well as suppressing other aspects (see, e.g., U.S. Pat. Nos. 6,039,969 and 6,200,592), IRMs may be used to treat many diseases. For example, the small molecule IRM imiquimod is useful for the treatment of external genital and perianal warts caused by human papillomavirus [see, e.g., Tomai et al, *Antiviral Research* 28(3): 253-64 (1995)]. Examples of other diseases that may be treated using IRMs include, but are not limited to, basal cell carcinoma, eczema, essential thrombocythaemia, hepatitis B, multiple sclerosis, neoplastic diseases, psoriasis, rheumatoid arthritis, type I herpes simplex, and type II herpes simplex.

IRM compounds also can modulate humoral immunity by stimulating antibody production by B cells. Further, various IRMs have been shown to be useful as vaccine adjuvants (see, e.g., U.S. Pat. Nos. 6,083,505 and 6,406,705).

SUMMARY OF THE INVENTION

It has now been found that IRMs, especially small molecule IRMs and agonists of TLR 2, 4, 6, 7, and 8, are surprisingly effective at stimulating an immune response when chemically or physically paired with an antigen to form an immunostimulatory composition. The immunostimulatory effect of a particular composition may be greater than the immunostimulatory effect of the same antigen and the same or a comparable IRM as that in the composition, but administered in an unpaired form.

The present invention provides an immunostimulatory composition that includes an immune response modifier (IRM) portion paired with an antigenic portion. In some embodiments, the IRM portion may be, or be derived from, an agonist of Toll-like receptor 2, Toll-like receptor 4, Toll-like receptor 6, Toll-like receptor 7, or Toll-like receptor 8. In other embodiments, the IRM portion may include, or be derived from, an imidazoquinoline amine; a tetrahydroimidazoquinoline amine; an imidazopyridine amine; an aryl ether-substituted imidazopyridine amine; a 1,2-bridged imidazoquinoline amine; a 6,7-fused cycloalkylimidazopyridine amine; an imidazonaphthyridine amine; a tetrahydroimidazonaphthyridine amine; an oxazoloquinoline amine; a thiazoloquinoline amine; an oxazolopyridine amine; a thiazolopyridine amine; an oxazolonaphthyridine amine; or a thiazolonaphthyridine amine. In still other embodiments, the IRM portion may include, or be derived from, an organic moiety having a molecular weight of less than about 1000 Daltons. The antigenic portion may include an amino acid sequence, a nucleotide sequence, a lipopolysaccharide, a prion, a bacterium, a virus, or a fungus.

In another aspect, the present invention provides a method of stimulating T cells of a patient. The method includes providing an immunostimulatory composition that includes an immune response modifier paired with an antigenic portion; permitting the immunostimulatory composition to bind to antigen-presenting cells, thereby activating the antigen-presenting cells; and permitting the activated antigen-presenting cells to stimulate the patient's T cells. The patient's T cells may be stimulated in vivo or in vitro.

In yet another aspect, the present invention provides a method of stimulating antibody-producing cells. The method includes providing an immunostimulatory composition that comprises an immune response modifier portion paired with an antigenic portion; and permitting the immunostimulatory composition to bind to the antibody-producing cells. The antibody-producing cells may be stimulated in vivo or in vitro. Various other features and advantages of the present invention should become readily apparent with reference to the following detailed description, examples, claims and appended drawings. In several places throughout the specification, guidance is provided through lists of examples. In

DETAILED DESCRIPTION OF ILLUSTRATIVE EMBODIMENTS OF THE INVENTION

Figure 1:
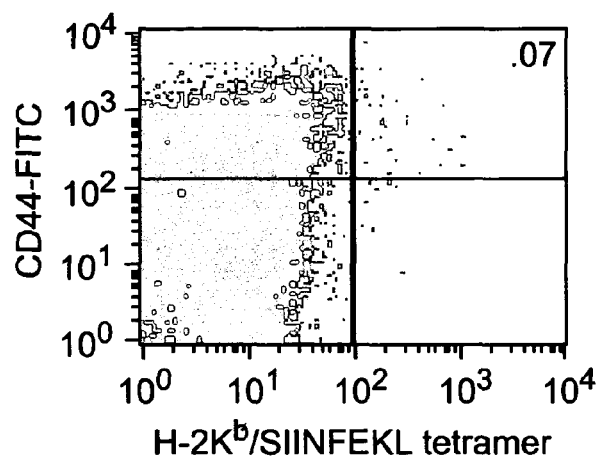
FIG. 1 shows the percentage of ovalbumin-specific activated CD8+ T cells generated by mice immunized with ovalbumin, as described in Example 4.

The present invention provides immunostimulatory compositions (ISCs), methods of making immunostimulatory compositions, methods of eliciting an immune response using immunostimulatory compositions, and methods of enhancing the immunostimulatory activity of an IRM by pairing the IRM with another immunostimulatory component (e.g., an antigen). The ISCs may be designed to elicit a cell-mediated immune response, a humoral immune response, or both.

As noted above, many IRMs can be used as a vaccine adjuvant to increase the immune response generated against one or more antigens also presented in the vaccine. Surprisingly, certain ISCs according to the present invention can provide an even greater immune response than a vaccine containing the same or a comparable IRM and the same antigen, but in an unpaired form. In one case, an ISC provided an immune response about five-fold greater than the immune response generated by a vaccine that included the same antigen and a comparable IRM.

As used herein, the term "paired" and variations thereof refer to components associated in some chemical or physical manner so that the components are not freely dispersible from one another. For example, two components may be covalently bound to one another so that the two components are incapable of separately dispersing or diffusing. Pairing also may be achieved by, for example, non-covalent affinity binding, ionic binding, hydrophilic or hydrophobic affinity, physical entrapment, and the like. Pairing is specifically distinguished from a simple mixture of antigen and adjuvant in a conventional vaccine. In a simple mixture, the components can be free to independently disperse within the vaccinated environment. As used herein, "paired" and variations thereof confers an understanding that paired components maintain a chemical or physical association after immunization.

The immune response modifier portion may be, or be derived from, any suitable IRM. Suitable IRMs include small organic molecules, i.e., molecules having a molecular weight of less than about 1000 Daltons, although in some embodiments the IRM may have a molecular weight of less than about 700 Daltons and in some cases the IRM may have a molecular weight from about 500 Daltons to about 700 Daltons. Suitable IRMs also include agonists of one or more of TLRs 2, 4, 6, 7, 8 and 9. In some embodiments, suitable IRMs include but are not limited to the small molecule IRM compounds described above and derivatives thereof. Suitable small molecule IRMs, having a 2-aminopyridine fused to a five membered nitrogen-containing heterocyclic ring, include but are not limited to imidazoquinoline amines including but not limited to amide-substituted imidazoquinoline amines, sulfonamide-substituted imidazoquinoline amines, urea-substituted imidazoquinoline amines, aryl ether-substituted imidazoquinoline amines, heterocyclic ether-substituted imidazoquinoline amines, amido ether-substituted imidazoquinoline amines, sulfonamido ether-substituted imidazoquinoline amines, urea-substituted imidazoquinoline ethers, and thioether-substituted imidazoquinoline amines; tetrahydroimidazoquinoline amines including but not limited to amide-substituted tetrahydroimidazoquinoline amines, sulfonamide-substituted tetrahydroimidazoquinoline amines, urea-substituted tetrahydroimidazoquinoline amines, aryl ether-substituted tetrahydroimidazoquinoline amines, heterocyclic ether-substituted tetrahydroimidazoquinoline amines, amido ether-substituted tetrahydroimidazoquinoline amines, sulfonamido ether-substituted tetrahydroimidazoquinoline amines, urea-substituted tetrahydroimidazoquinoline ethers, and thioether-substituted tetrahydroimidazoquinoline amines; imidazopyridine amines including but not limited to amide-substituted imidazopyridine amines, sulfonamido-substituted imidazopyridine amines, urea-substituted imidazopyridine amines; aryl ether-substituted imidazopyridine amines, heterocyclic ether-substituted imidazopyridine amines, amido ether-substituted imidazopyridine amines, sulfonamido ether-substituted imidazopyridine amines, urea-substituted imidazopyridine ethers, and thioether-substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; and thiazolonaphthyridine amines.

Additional suitable small molecule IRMs include the certain purine derivatives, certain imidazoquinoline amide derivatives, certain benzimidazole derivatives, and certain derivatives of a 4-aminopyrimidine fused to a five membered nitrogen containing heterocyclic ring (e.g., adenine derivatives) described above.

Other suitable IRMs include the CpGs and other IRM nucleotide sequences that lack CpG described above.

The antigenic portion can include any material that raises a cell-mediated immune response, a humoral immune response, or both. Suitable antigenic materials include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived immunogens, toxins or toxoids.

Diseases for which immunostimulatory compositions of the present invention may be used as treatments include, but are not limited to:

(a) viral diseases, such as genital warts, common warts, plantar warts, hepatitis B, hepatitis C, herpes simplex virus type I and type II, molluscum contagiosum, variola, HIV, CMV, VZV, rhinovirus, adenovirus, coronavirus, influenza, para-influenza;

(b) bacterial diseases, such as tuberculosis, and mycobacterium avium, leprosy;

(c) other infectious diseases, such as fungal diseases, chlamydia, candida, aspergillus, cryptococcal meningitis, pneumocystis carnii, cryptosporidiosis, histoplasmosis, toxoplasmosis, trypanosome infection, leishmaniasis;

(d) neoplastic diseases, such as intraepithelial neoplasias, cervical dysplasia, actinic keratosis, basal cell carcinoma, squamous cell carcinoma, hairy cell leukemia, Karposi's sarcoma, melanoma, renal cell carcinoma, myelogeous leukemia, multiple myeloma, non-Hodgkin's lymphoma, cutaneous T-cell lymphoma, and other cancers;

(e) TH-2 mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing would healing, including chronic wounds; and (f) as a vaccine adjuvant for use in conjunction with any material that raises either humoral and/or cell mediated immune response, such live viral and bacterial immunogens and inactivated viral, tumor-derived, protozoal, organism-derived, fungal, and bacterial immunogens, toxoids, toxins, polysaccharides, proteins, glycoproteins, peptides, cellular vaccines, DNA vaccines, recombinant proteins, glycoproteins, and peptides, and the like, for use in connection with, e.g., BCG, cholera, plague, typhoid, hepatitis A, B, and C, influenza A and B. parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, and yellow fever.

Immunostimulatory compositions of the invention include an effective amount of biological activity of both the immune response modifier portion and the antigenic portion. An effective amount of biological activity of the immune response portion ("IRM activity") includes one or more of the following: an increase in cytokine production by T cells, activation of T cells specific to an antigen, and activation of dendritic cells. An effective amount of biological activity of the antigenic portion ("antigenic activity") includes one or more of the following: generation of antibodies specific to the antigen by B cells and generation of antigen-presenting cells that present the antigen. Immunostimulatory compositions of the present invention may be combined with a pharmaceutically acceptable carrier, one or more excipients, or some combination of the foregoing in order to form a pharmaceutical composition.

Although the exact amount of active compound used in a pharmaceutical composition of the invention will vary according to factors known to those of skill in the art, such as the physical and chemical nature of the immunostimulatory composition, the nature of the carrier, the nature of the subject's immune system (e.g., suppressed, compromised, stimulated), and the intended dosing regimen, it is anticipated that pharmaceutical compositions of the invention will contain sufficient immune response modifier portion to provide a dose of about 100 ng/kg to about 50 mg/kg, preferably about 10 µg/kg to about 5 mg/kg, of IRM to the subject.

A variety of dosage forms may be used, such as tablets, lozenges, capsules, parenteral formulations, syrups, creams, ointments, aerosol formulations, transdermal patches, transmucosal patches and the like.

Pharmaceutical compositions of the invention can be administered as the single therapeutic agent in a treatment regimen, or the pharmaceutical composition may be administered in combination with another pharmaceutical composition or with other active agents, including additional immune response modifiers, antivirals, antibiotics, antibodies, proteins, peptides, oligonucleotides, etc.

In some embodiments, the immunostimulatory immune response modifier portion may be covalently coupled to the antigenic portion to form an immunostimulatory conjugate. As used herein, "covalently coupled" refers to direct and indirect coupling of two components exclusively through covalent bonds. Direct covalent coupling may involve direct covalent binding between an atom of the immune response modifier portion and an atom of the antigenic portion. Alternatively, the covalent coupling may occur through a linking group covalently attached to the IRM portion, the antigenic portion, or both, that facilitates covalent coupling of the IRM portion and the antigenic portion. Indirect covalent coupling may include a third component such as, for example, a solid support to which the immune response modifier portion and the antigenic portion are separately covalently attached. Also, "covalently coupled" and "covalently attached" are used interchangeably.

An immunostimulatory conjugate can include an immune response modifier moiety as the IRM portion and an antigen-containing moiety as the antigenic portion. When synthesizing an immunostimulatory conjugate, each of the immune response modifier moiety, the linking group, and the antigen-containing moiety may be selected so that the resulting immunostimulatory conjugate possesses an effective amount of IRM activity and an effective amount of antigenic activity.

The linking group can be any suitable organic linking group that allows the antigen-containing moiety to be covalently coupled to the immune response modifier moiety while preserving an effective amount of IRM activity and antigenic activity. In some embodiments, the linking group may be selected to create sufficient space between the active core of the immune response modifier moiety and the antigen-containing moiety that the antigen-containing moiety does not interfere with a biologically effective interaction between the active core and T cells that results in IRM activity such as cytokine production.

The linking group includes a reactive group capable of reacting with the antigen to form a covalent bond. Suitable reactive groups include those discussed in Hermanson, G. (1996), *Bioconjugate Techniques*, Academic Press, Chapter 2 "The Chemistry of Reactive Functional Groups", 137-166. For example, the linking group may react with a primary amine (e.g., an N-hydroxysuccinimidyl ester or an N-hydroxysulfosuccinimidyl ester); it may react with a sulfhydryl group (e.g., a maleimide or an iodoacetyl), or it may be a photoreactive group (e.g. a phenyl azide including 4-azidophenyl, 2-hydroxy-4-azidophenyl, 2-nitro-4-azidophenyl, and 2-nitro-3-azidophenyl).

A chemically active group accessible for covalent coupling to the linking group includes groups that may be used directly for covalent coupling to the linking group or groups that may be modified to be available for covalent coupling to the linking group. For example, suitable chemically active groups include but are not limited to primary amines and sulfhydryl groups. Because certain antigen-containing moieties, e.g., proteins and other peptides, may include a plurality of chemically active groups, certain ISCs according to the present invention may include a plurality of IRM moieties conjugated to a particular antigen-containing moiety.

Methods of Making Immunostimulatory Conjugates

Immunostimulatory conjugates according to the present invention generally may be prepared by reacting an immune response modifier with a crosslinker and then reacting the resulting intermediate with an antigen. Many crosslinkers suitable for preparing bioconjugates are known and many are commercially available. See for example, Hermanson, G. (1996) *Bioconjugate Techniques*, Academic Press.

Immunostimulatory conjugates according to the present invention also may be prepared, for example, according to the method shown in Reaction Scheme I in which the antigen-containing moiety is linked to the IRM moiety through $R_1$. In step (1) of Reaction Scheme I a compound of Formula III is reacted with a heterobifunctional cross-linker of Formula IV to provide a compound of II. $R_A$ and $R_B$ each contain a functional group that is selected to react with the other. For example, if $R_A$ contains a primary amine, then a heterobifunctional cross-linker may be selected in which $R_B$ contains an amine-reactive functional group such as an N-hydroxysulfosuccinimidyl ester. $R_A$ and $R_B$ may be selected so that they react to provide the desired linker group in the conjugate.

Methods for preparing compounds of Formula III where $R_4$ contains a functional group are known. See for example, U.S. Pat. Nos. 4,689,338; 4,929,624; 5,268,376; 5,389,640; 5,352,784; 5,494,916; 4,988,815; 5,367,076; 5,175,296; 5,395,937; 5,741,908; 5,693,811; 6,069,149; 6,194,425; and 6,331,539 and International Publications WO 00/76505; WO 00/76518; WO 02/46188; WO 02/46189; WO 02/46190; WO 02/46191; WO 02/46192; WO 02/46193; and WO 02/46194.

Many heterobifunctional cross-linkers are known and many are commercially available. See for example, Hermanson, G. (1996), *Bioconjugate Techniques*, Academic Press, Chapter 5 "Heterobifunctional Cross-Linkers", 229-285. The reaction generally can be carried out by combining a solution of the compound of Formula III in a suitable solvent such as N,N-dimethylformamide with a solution of the heterobifunctional cross-linker of Formula IV in a suitable solvent such as N,N-dimethylformamide. The reaction may be run at ambient temperature. The product of Formula II may then be isolated using conventional techniques.

In step (2) of Reaction Scheme I a compound of Formula III that contains reactive group $Z_A$ is reacted with the antigen to provide the immunostimulatory conjugate of Formula I. The reaction generally can be carried out by combining a solution of the compound of Formula II in a suitable solvent such as dimethyl sulfoxide with a solution of the antigen in a suitable buffer such as PBS. The reaction may be run at ambient temperature or at a reduced temperature (~4° C.). If $Z_A$ is a photoreactive group such as a phenyl azide then the reaction mixture will be exposed to long wave UV light for a length of time adequate to effect cross-linking (e.g., 10-20 minutes). The average number of immune response modifier moieties per antigen moiety may be controlled by adjusting the amount of compound of Formula II used in the reaction. The immune response conjugate of Formula I may be isolated and purified using conventional techniques.

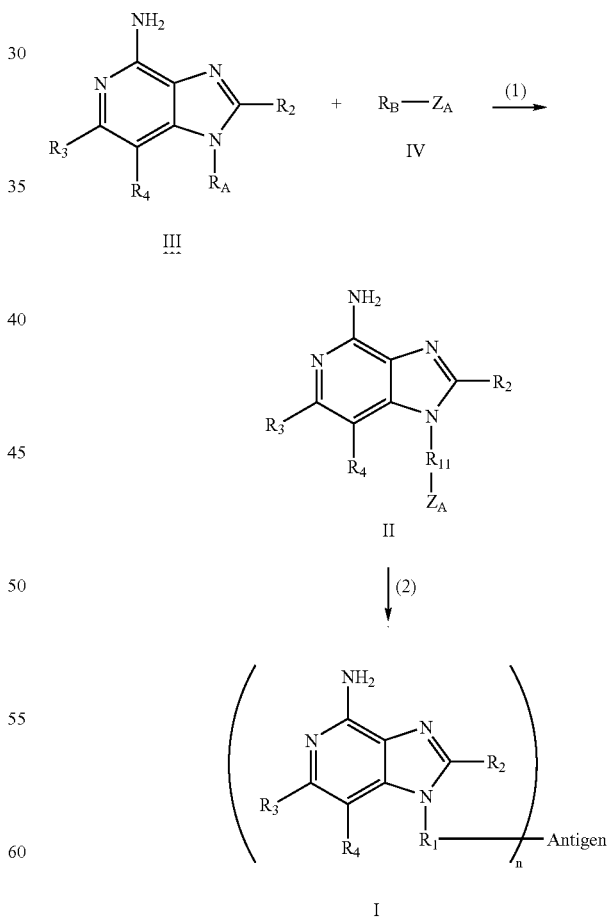

Alternatively, a compound of Formula II may be synthesized without using a heterobifunctional cross-linker. So long as the compound of Formula II contains the reactive group $Z_A$, it may be reacted with the antigen using the method of step (2) above to provide an immunostimulatory conjugate.

As used herein, the terms "alkyl", "alkenyl" and the prefix "alk-" include straight chain, branched chain, and cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, and adamantyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The aryl, heteroaryl, and heterocyclyl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonythio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylaamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted", then those groups can also be substituted by one or more of the above-enumerated substituents.

Certain substituents are generally preferred. For example, preferred $R_2$ groups include hydrogen, alkyl groups having 1 to 4 carbon atoms (i.e., methyl, ethyl, propyl, isopropyl, n-butyl, sec-butyl, isobutyl, tert-butyl, and cyclopropylmethyl), and alkoxyalkyl groups (e.g., methoxyethyl and ethoxymethyl). Preferably $R_3$ and $R_4$ are independently hydrogen or methyl or $R_3$ and $R_4$ join together to form a benzene ring, a pyridine ring, a 6-membered saturated ring or a 6-membered saturated ring containing a nitrogen atom. One or more of these preferred substituents, if present, can be present in the compounds of the invention in any combination.

In some embodiments, the immunostimulatory conjugates may include a solid support structure to which both the antigenic portion and the IRM portion are attached. In some embodiments, the IRM portion, antigenic portion, or both may be covalently attached to the solid support using a linking group such as those described above. The solid support may include, for example, agarose beads, gold particles, and the like. The solid support may then be used to co-deliver the attached IRM portion and antigenic portion to the appropriate target cell population. Methods for attaching biomolecules to solid supports are known in the art. Protocols for immobilizing biomolecules on solid supports are well known in the art and suitable reagents are available from commercial sources.

Immunostimulatory compositions according to the present invention may contain chemical associations between the IRM portion and the antigenic portion other than covalent coupling. For example, an ISC may include an affinity interaction between the antigenic portion and the IRM portion. Avidin-biotin affinity represents one example of a non-covalent interaction that may be utilized to pair an antigenic portion with an IRM portion. A biotin molecule may be chemically attached to an antigen via one of a number of functional groups present on amino acids in, for example, a proteinaceous antigen (e.g., primary amines or sulfhydryl groups). An IRM portion may be conjugated to an avidin molecule by similar chemical means. The IRM portion and the antigenic portion may then be paired by the avidin-biotin affinity interaction. Methods for biotinylating proteins and linking chemical groups to avidin are well known to one of skill in the art. Alternative affinity interactions that may be useful for making ISCs include, for example, antigen/antibody interactions, glycoprotein/lectin interactions.

Immunostimulatory compositions also may be formed by ionic interactions between an IRM portion and an antigenic portion. For example, an IRM portion, an antigenic portion, or both, may be chemically modified to contain oppositely charged components. The oppositely charged IRM portion and antigenic portion may then be incubated together to allow for ionic interaction between the two entities. The resulting ISC may then be administered to a subject or a cell population, resulting in the co-delivery of both the IRM and the antigen to the target cells.

As in the case of covalently linked ISCs, ISCs in which the IRM portion and the antigenic portion are paired non-covalently can include a solid support.

Methods of Eliciting Immune Responses Using Immunostimulatory Conjugates

Immunostimulatory compositions according to the present invention may be used to elicit immune responses from cells of the immune system in vitro or in vivo. Thus, an ISC according to the present invention may be useful as a component of a vaccine or as an immunostimulatory factor used in in vitro cell culture of T cells or B cells. Indeed, IRMs may be more potent immunostimulatory factors when delivered as part of an ISC according to the present invention compared to being delivered as an unpaired vaccine adjuvant. When used to elicit immune responses in vitro, the immune cells activated in vitro may be reintroduced into a patient. Alternatively, factors secreted by the activated immune cells, e.g., antibodies, cytokines, and the like, may be collected for investigative, diagnostic, and/or therapeutic uses.

Unless otherwise noted, a host may be immunized subcutaneously or intraperitoneally. After a sufficient time to allow the host to generate an immune response to the ISC, immune cells appropriate for the immunization site are harvested. For example, lymph nodes may be harvested from a host that had been immunized subcutaneously. Spleen cells may be harvested from a host immunized peritoneally. For some hosts, cell harvesting may include sacrificing the hosts. In other cases, cell harvesting may include a biopsy or surgical removal of an appropriate tissue.

Figure 2:
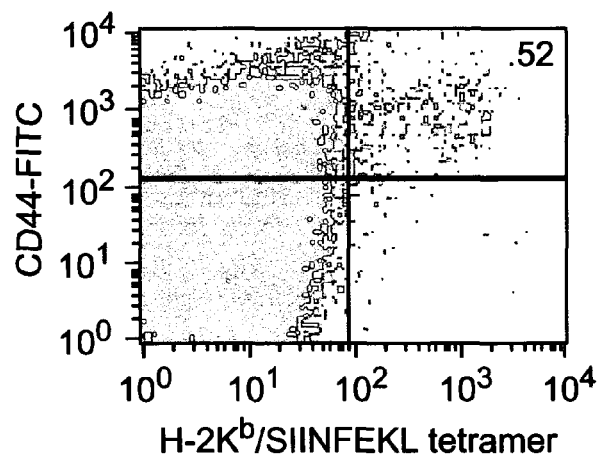
FIG. 2 shows the percentage of ovalbumin-specific activated CD8+ T cells generated by mice immunized subcutaneously with an IRM-ovalbumin conjugate, as described in Example 4.
Figure 3:
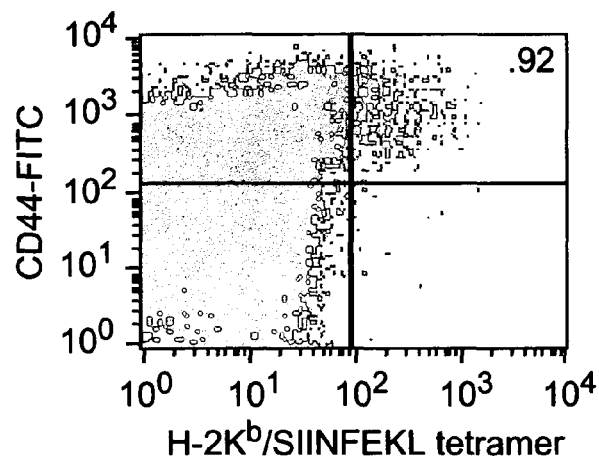
FIG. 3 shows the percentage of ovalbumin-specific activated CD8+ T cells generated by mice immunized intraperitoneally with an IRM-ovalbumin conjugate, as described in Example 4.
Figure 15:
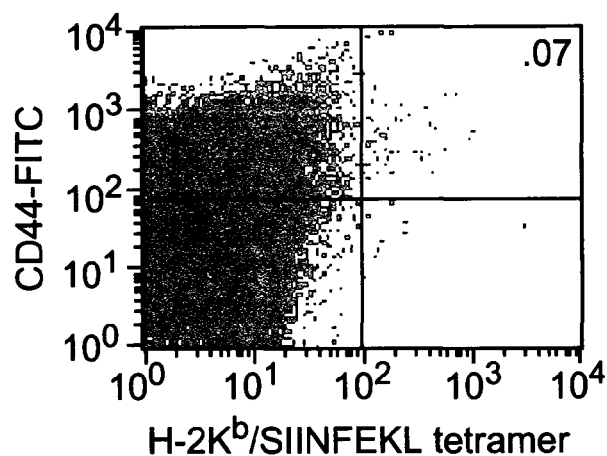
FIG. 15 shows expansion of antigen-specific CD8+ T cells after immunization with ovalbumin, as described in Example 11.
Figure 16:
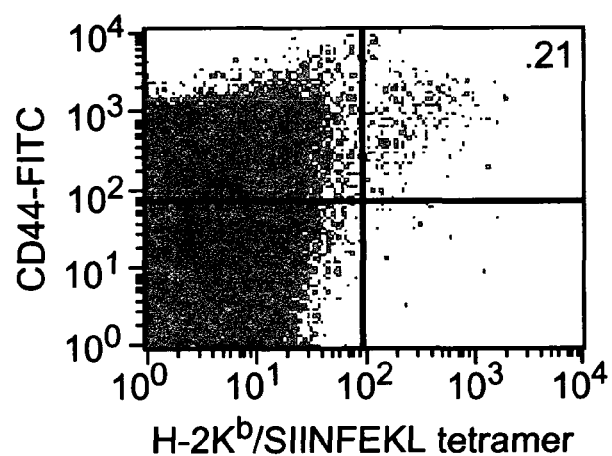
FIG. 16 shows expansion of antigen-specific CD8+ T cells in one subject after immunization with a colloidal suspension of IRM and ovalbumin, as described in Example 11.
Figure 17:
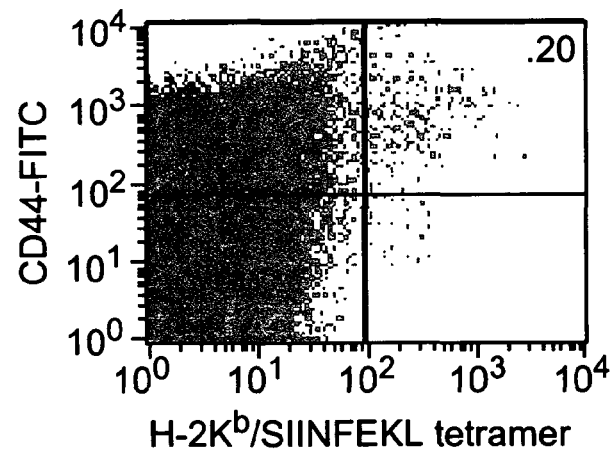
FIG. 17 shows expansion of antigen-specific CD8+ T cells in a second subject after immunization with a colloidal suspension of IRM and ovalbumin, as described in Example 11.

In one embodiment, ISCs may be used to induce the proliferation of antigen-specific T cells. A host (e.g., a mouse) may be immunized with an ISC that includes a particular antigen. After sufficient incubation in the host, certain T cells (e.g., CD8$^+$ T cells) will mature to antigen-specific T cells in response to the immunization. A greater percentage of T cells will be antigen-specific in hosts immunized with ISCs compared to hosts immunized with only antigen (FIGS. 1-3). The ISC may be paired by covalently coupling the IRM portion and the antigenic portion (FIGS. 1-3) or, alternatively, by a non-covalent pairing such as, for example, a colloidal suspension (FIGS. 15-17).

Figure 7:
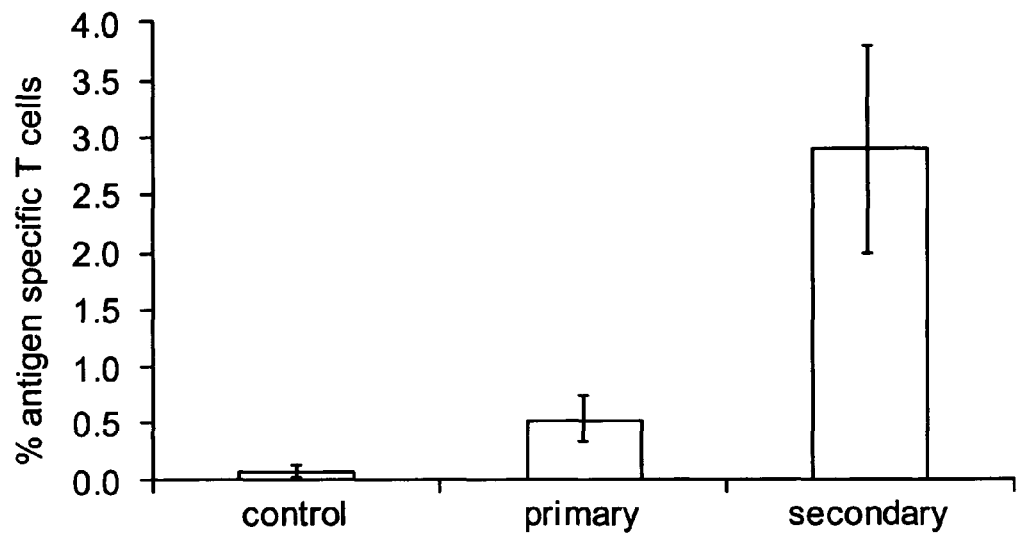
FIG. 7 shows an increase in the antigen-specific immune response upon providing a secondary immunization with an IRM-ovalbumin conjugate, as described in Example 6.

If the antigen is a protein (e.g., ovalbumin), it may not be necessary that the ISC include the entire protein. For example, an immunodominant peptide from the protein may be all that is required to induce development of T cells specific to the full protein antigen. Moreover, a booster immunization, e.g., 15 days after the initial immunization, can augment the induction of antigen-specific T cells (FIG. 7).

Immunization of a host with ISCs may be used to elicit an antigen-specific response in CD8$^+$ cytotoxic T lymphocytes (CTLs). Such a response may be directed against many conditions including, but not limited to, tumors and virally-infected cell populations. ISCs also may be administered prophylactically to provide a host with a protective CTL immunity directed against future tumors or viral infections.

In another embodiment, ISCs may be used to induce cytokine production by antigen-specific T cells in vitro. Appropriate tissue from an immunized host may be harvested and cultured in vitro with antigen, thereby inducing production of one or more cytokines (e.g., IFN-γ, see FIGS. 4-6). Again, in cases where the antigen is a protein, an immunodominant peptide from the antigen protein may be all that is required to induce the antigen-specific T cells in cell culture to produce and secrete the cytokines.

Figure 8:
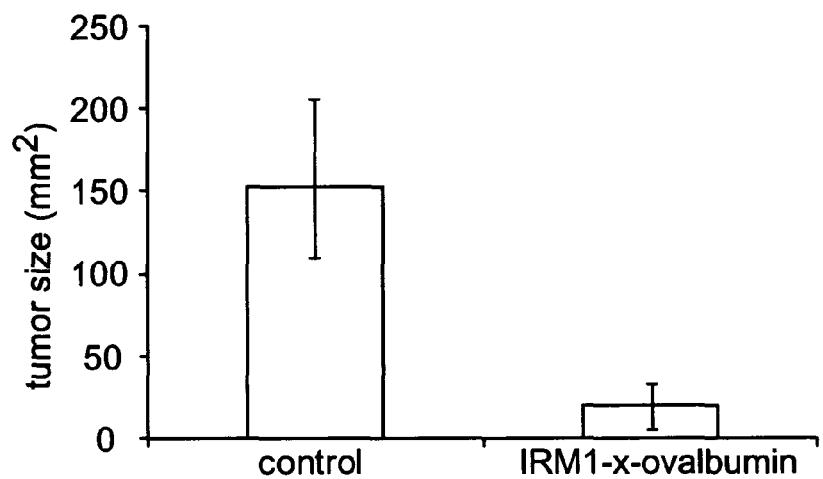
FIG. 8 shows reduction in tumor size after immunization with a tumor-specific IRM-antigen conjugate, as described in Example 7.
Figure 10:
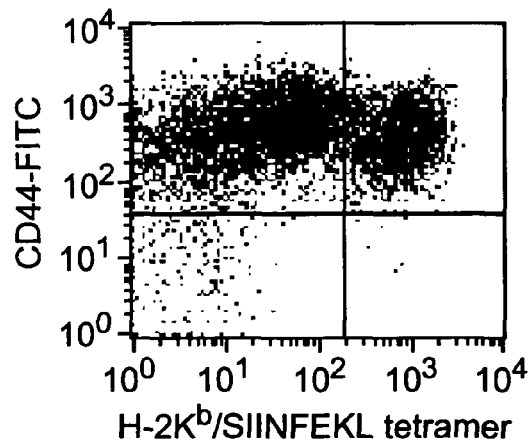
FIG. 10 shows expansion of activated tumor antigen-specific CD8+ T cells in the tumor after immunization with an IRM-tumor antigen conjugate, as described in Example 8.

In another embodiment, ISCs may be used to inhibit tumor growth in vivo. Hosts having tumor cells expressing a particular antigen may be immunized with ISCs that contain the antigen. In some embodiments, the initial immunization may be boosted with a second immunization. Tumors harvested from hosts immunized with ISC containing the antigen were generally smaller than the tumors harvested from hosts immunized with only the antigen (FIG. 8). Moreover, analysis of the tumors showed that tumors harvested from hosts immunized with ISC contained a higher percentage of antigen-specific T cells that did tumors harvested from hosts immunized with only the antigen (FIG. 10).

Figure 11:
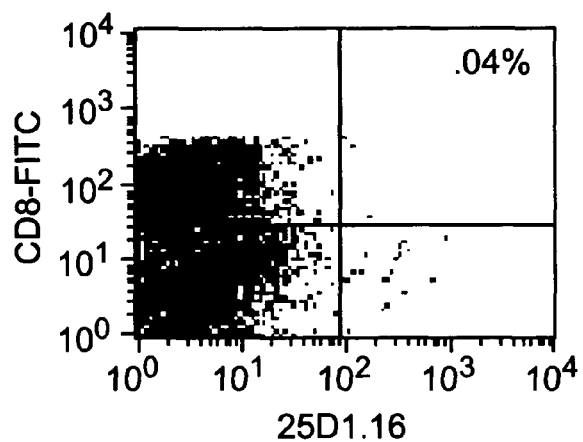
FIG. 11 shows the percentage of antigen presenting cells that are presenting $K^b$/SIINFEKL after immunization with ovalbumin, as described in Example 9.
Figure 12:
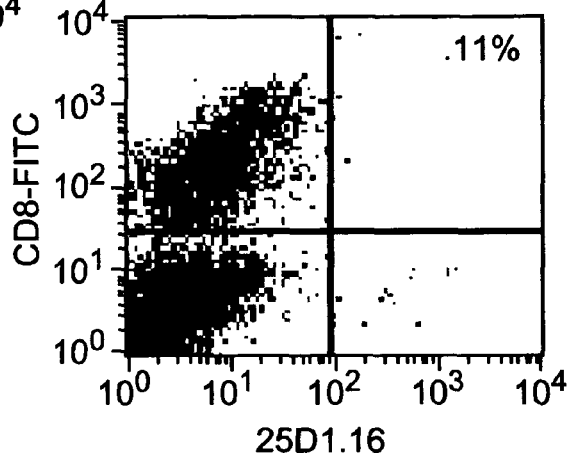
FIG. 12 the percentage of antigen presenting cells that are presenting $K^b$/SIINFEKL after immunization with ovalbumin plus non-conjugated IRM, as described in Example 9.
Figure 13:
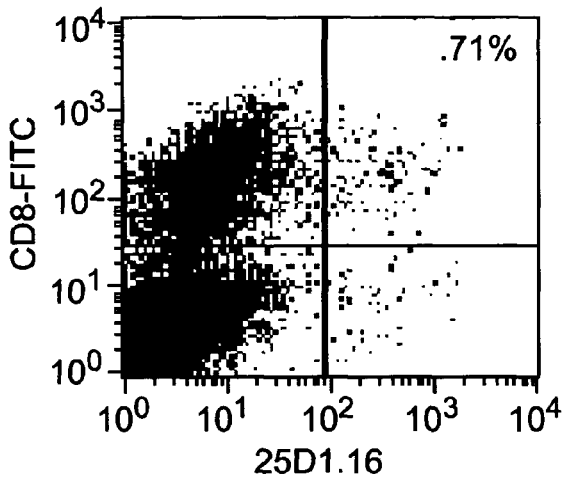
FIG. 13 the percentage of antigen presenting cells that are presenting $K^b$/SIINFEKL after immunization with IRM-ovalbumin conjugate, as described in Example 9.

In yet another embodiment, ISCs may be used to induce antigen-presenting cells (APCs, e.g., dendritic cells) to present peptides from the antigen within MHC class I complexes at their cell surfaces. Hosts may be immunized intravenously to induce this type of response. The response may be verified by harvesting and analyzing spleen cells for APCs presenting antigen/MHC class I complexes (FIGS. 11-13).

In an alternative embodiment, ISCs may be used to develop antigen-specific T cells in vitro. For example, bone marrow cells may be harvested from a patient having a tumor that expresses a particular antigen. The harvested cells may be cultured in vitro with an ISC containing the antigen expressed by the tumor. Once again, if the antigen is a protein, the ISC may need only include an immunodominant peptide of the protein. Antigen-specific T cells that develop in vitro in response to incubation with the ISC may be reintroduced to the patient.

Figure 14:
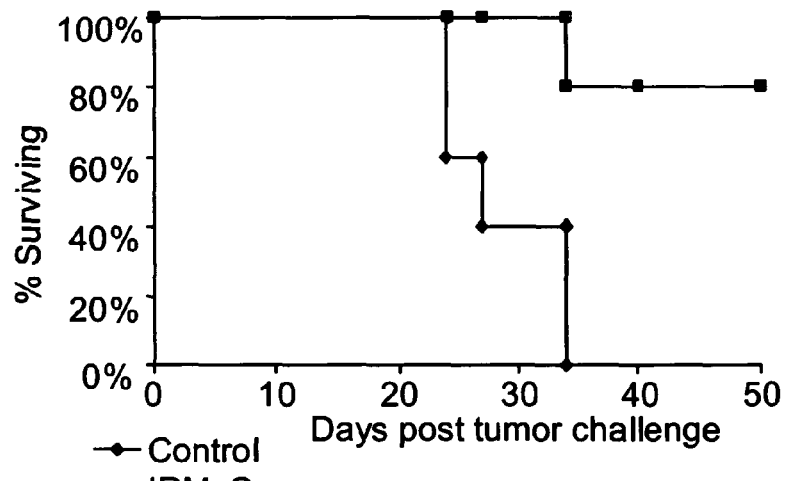
FIG. 14 shows survival rates of mice immunized with ovalbumin or an IRM-ovalbumin conjugate after challenge with ovalbumin-expressing tumor cells, as desribed in Example 10.

In yet another alternative embodiment, an ISC may be administered to a subject having a tumor to increase the likelihood, duration, or both, of survival. An ISC including a tumor-specific antigenic portion administered to a mice challenged with melanoma cells provided increased survival compared to mice immunized with only tumor antigen (FIG. 14).

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

Preparation of IRM Compounds

IRM Compound 1 (IRM1): N-[6-({2-[4-amino-2-(ethoxymethyl)-1H-imidazo[4,5c]quinolin-1-yl]-1,1-dimethylethyl}amino)-6-oxohexyl]-4-azido-2-hydroxybenzamide

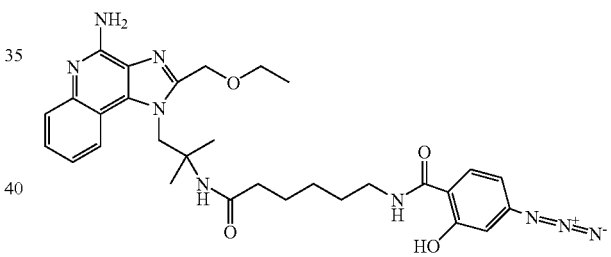

Part A

A stirred solution of 4-chloro-3-nitroquinoline (17.3 g, 83.2 mmol) in 200 mL of anhydrous $CH_2Cl_2$, under $N_2$, was treated with triethylamine (23.2 mL, 166.4 mmol) and 1,2-diamino-2-methylpropane (9.57 mL, 91.5 mmol). After stirring overnight, the reaction mixture was diluted with 800 mL of $CHCl_3$, washed with $H_2O$ (3×300 mL) and brine (300 mL). The organic portion was dried over $Na_2SO_4$ and concentrated to give 2-methyl-$N^1$-(3-nitroquinolin-4-yl)propane-1,2-diamine (21.0 g) as a bright yellow solid.

Part B

A solution of 2-methyl-$N^1$-(3-nitroquinolin-4-yl)propane-1,2-diamine (2.60 g, 10.0 mmol) in 50 mL of tetrahydrofuran (THF), under $N_2$, was cooled to 0° C. and treated with 10 mL of 1N NaOH solution. Di-tert-butyl dicarbonate (2.18 g, 10.0 mmol) was then added to the rapidly stirred solution. The reaction mixture was then allowed to warm to ambient temperature and was stirred overnight. An additional 400 mg of di-tert-butyl dicarbonate was added and stirring was continued for 3 days. The reaction was then treated with ethyl acetate (200 mL) and washed with $H_2O$ (2×) and brine. The organic portion was dried over $Na_2SO_4$ and concentrated to give a yellow solid that was triturated with 10% EtOAc/hexanes. The solid was isolated by filtration and dried under vacuum overnight to give tert-butyl 1,1-dimethyl-2-[(3-nitroquinolin-4-yl)amino]ethylcarbamate (2.80 g) as a yellow powder.

Part C

A solution of tert-butyl 1,1-dimethyl-2-[(3-nitroquinolin-4-yl)amino]ethylcarbamate (3.50 g, 9.72 mmol), in 150 mL of toluene was treated with 0.3 g of 5% Pt on carbon and shaken under $H_2$ (3 atm, 3 Kg/cm$^2$) for 6 hours. The solution was then filtered through a Celite pad and concentrated to give 3.04 g of crude tert-butyl 2-[(3-aminoquinolin-4-yl]-1,1-dimethylethylcarbamate as a light orange foam.

Part D

A solution of tert-butyl 2-[(3-aniinoquinolin-4-yl]-1,1-dimethylethylcarbamate (3.04 g, 9.21 mmol) in 50 mL of $CH_2Cl_2$ was cooled to 0° C. and treated with triethylamine (1.41 mL, 10.13 mmol) and ethoxyacetyl chloride (1.02 mL, 10.17 mmol). After 2 hours, the reaction mixture was concentrated under reduced pressure. The resulting syrup was taken up in 100 mL of EtOH and treated with 4.5 mL of triethylamine. The solution was heated to reflux overnight. The reaction mixture was concentrated and taken up in 100 mL of $CH_2Cl_2$ and washed with $H_2O$ (2×) and brine. The organic portion was dried over $Na_2SO_4$ and concentrated. The resulting syrup was purified by column chromatography ($SiO_2$, 80% EtOAc/hexanes) to give tert-butyl 2-[2-(ethoxymethy)-1H-imidazo[4,5-c]quinolin-1-yl]-1,1-dimethylethylcarbamate (1.57 g) as a peach colored foam.

Part E

A solution of tert-butyl 2-[2-(ethoxymethy)-1H-imidazo[4,5-c]quinolin-1-yl]-1,1-dimethylethylcarbamate (1.57 g, 3.94 mmol) in 30 mL of $CH_2Cl_2$ was treated with 3-chloroperoxybenzoic acid (77%, 1.01 g, 4.57 mmol). After stirring for 2 hours, the reaction mixture was treated with 30 mL of additional $CH_2Cl_2$ and was washed with 1% $Na_2CO_3$ solution (2×30 mL), $H_2O$ and brine. The organic portion was then dried over $Na_2SO_4$ and concentrated to give tert-butyl 2-[2-(2-(ethoxymethyl)-5-oxido-1H-imidazo[4,5-c]quinolin-1-yl]-1,1-dimethylethylcarbamate (1.58 g) as a light brown foam.

Part F

A solution of tert-butyl 2-[2-(2-(ethoxymethyl)-5-oxido-1H-imidazo[4,5-c]quinolin-1-yl]-1,1-dimethylethylcarbamate (1.57 g, 3.79 mmol) in 20 mL of 1,2-dichloroethane was heated to 70° C. and treated with 2 mL of concentrated $NH_4OH$ solution. To the rapidly stirred solution was added solid p-toluenesulfonyl chloride (795 mg, 4.17 mmol). The reaction mixture was then sealed in a pressure vessel and heating was continued for 2 hours. The reaction mixture was then cooled and treated with 50 mL of $CHCl_3$. The reaction mixture was then washed with $H_2O$, 1% $Na_2CO_3$ solution (3×) and brine. The organic portion was dried over $Na_2SO_4$ and concentrated to give the product as a light brown oil. The resulting oil was purified by column chromatography ($SiO_2$, 2-5% MeOH/$CHCl_3$) to give tert-butyl 2-[4-amino-2-(ethoxymethyl)-1H-imidazo[4,5-c]quinolin-1-yl]-1,1-dimethylethylcarbamate (1.26 g) as a light yellow foam.

Part G

Tert-butyl 2-[4-amino-2-(ethoxymethyl)-1H-imidazo[4,5-c]quinolin-1-yl]-1,1-dimethylethylcarbamate (1.26 g, 3.05 mmol) was dissolved in 10 mL of EtOH and treated with 10 mL of 2 M HCl in EtOH. After heating at reflux for 2 hours, the reaction mixture was cooled and concentrated under reduced pressure. The resulting yellow solid was dissolved in 50 mL of $H_2O$ and extracted with $CHCl_3$ (20 mL). The organic layer was discarded and the aqueous portion was made basic (pH~12) by addition of concentrated $NH_4OH$ solution. This was then extracted with $CHCl_3$ (4×20 mL) and the combined organic portions were dried with $Na_2SO_4$ and concentrated to give 1-(2-amino-2-methylpropyl)-2-(ethoxymethyl)-1H-imidazo[4,5-c]quinoline-4-amine (808 mg) as a light brown powder. m.p. 161.0-162.0° C.;

MS m/z 314(M+H); $^1$H NMR (300 MHz, $d_6$-DMSO) δ 8.30 (d, J=7.7 Hz, 1H), 7.59 (dd, J=1.2, 8.3 Hz, 1H), 7.40 (ddd, J=1.0, 7.2, 8.1 Hz, 1H), 7.21 (ddd, J=1.2, 7.0, 8.2 Hz, 1H), 6.57 (s, 2H), 4.94 (br s, 2H), 4.61 (br s, 2H), 3.52 (q, J=7.0 Hz, 2H), 1.61 (s, 2H), 1.31 (t, J=7.0 Hz, 3H), 1.07 (s, 6H);

$^{13}$C NMR (75 MHz, $d_6$-DMSO) δ 152.4, 151.1, 145.7, 134.3, 126.8, 126.7, 121.7, 120.8, 115.7, 65.6, 65.2, 55.8, 52.5, 29.2, 15.4. Anal. Calcd for $C_{17}H_{23}N_5O$: % C, 65.15; % H, 7.40; % N, 22.35. Found: % C, 65.04; % H, 7.52; % N, 22.07.

Part H

Under a nitrogen atmosphere, a solution of N-hydroxysulfosuccinimidyl (azidosalicylamido)hexanoate (100 mg, 0.204 mmol of Sulfo-LC-NHS-ASA from Pierce Biotechnology, Inc, Rockford, Ill, USA) in N,N-dimethylformamide DMF, (2-4 mL) was added to a solution of 1-(2-amino-2-methylpropyl)-2-(ethoxymethyl)-1H-imidazo[4,5-c]quinoline-4-amine (63 mg, 0.201 mmol) in DMF (5 mL). The reaction mixture was stirred under nitrogen in a foil wrapped vessel. After 2 days an additional 50 mg of N-hydroxysulfosuccinimidyl (azidosalicylamido)hexanoate was added. After about a week the reaction mixture was concentrated under reduced pressure at 55° C. The residue was partitioned between dichloromethane containing a small amount of methanol and water. The organic layer was separated and concentrated under reduced pressure. The residue was purified by flash chromatography (2×15 cm $SiO_2$ eluting with 6% methanol in chloroform) to provide 53 mg of product as a colorless glass. The glass was transferred using dichloromethane to a conical flask and then concentrated to provide a foam. The foam was dried overnight under high vacuum to provide 48 mg of a white crystalline solid. Analysis by NMR indicated the presence of dichloromethane so the material was dried overnight under high vacuum and then in a vacuum oven at 50° C. for 5 hours. Analysis by HPLC indicated a purity of >93%.

IRM Compound 2 (IRM2): N-{6-[(2-{2-[4-amino-2-(2-methoxyethyl)-1H-imidazo[4,5-c]quinolin-1-yl]ethoxy}ethyl)amino]-6-oxohexyl}-4-azido-2-hydroxybenzamide

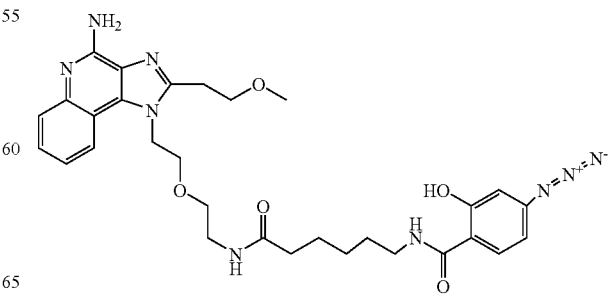

Part A

A solution of 2-(2-aminoethoxy)ethanol (29.0 g, 0.276 mol) in 180 mL of tetrahydrofuran (THF), under $N_2$, was cooled to 0° C. and treated with 140 mL of 2N NaOH solution. A solution of di-tert-butyl dicarbonate (60.2 g, 0.276 mol) in 180 mL of THF was then added dropwise over 1 h to the rapidly stirred solution. The reaction mixture was then allowed to warm to room temperature and was stirred an additional 18 hours. The THF was then removed under reduced pressure and the remaining aqueous slurry was brought to pH 3 by addition of 150 mL of 1M $H_2SO_4$ solution. This was then extracted with ethyl acetate (300 mL, 100 mL) and the combined organic layers were washed with $H_2O$ (2×) and brine. The organic portion was dried over $Na_2SO_4$ and concentrated to give tert-butyl 2-(2-hydroxyethoxy)ethylcarbamate as a colorless oil (47.1 g).

Part B

A rapidly stirred solution of tert-butyl 2-(2-hydroxyethoxy)ethylcarbamate (47.1 g, 0.230 mol) in 1 L of anhydrous $CH_2Cl_2$ was cooled to 0° C. under $N_2$ and treated with triethylamine (48.0 mL, 0.345 mol). Methanesulfonyl chloride (19.6 mL, 0.253 mol) was then added dropwise over 30 min. The reaction mixture was then allowed to warm to room temperature and was stirred an additional 22 hours. The reaction was quenched by addition of 500 mL saturated $NaHCO_3$ solution and the organic layer was separated. The organic phase was then washed with $H_2O$ (3×500 mL) and brine. The organic portion was dried over $Na_2SO_4$ and concentrated to give 2-{2-[(tert-butoxycarbonyl)amino]ethoxy}ethyl methanesulfonate as a brown oil (63.5 g).

Part C

A stirred solution of 2-{2-[(tert-butoxycarbonyl)amino]ethoxy}ethyl methanesulfonate (63.5 g, 0.224 mol) in 400 mL of N,N-dimethylformaniide (DMF) was treated with $NaN_3$ (16.1 g, 0.247 mol) and the reaction mixture was heated to 90° C. under $N_2$. After 5 hours, the solution was cooled to room temperature and treated with 500 mL of cold $H_2O$. The reaction mixture was then extracted with $Et_2O$ (3×300 mL). The combined organic extracts were washed with $H_2O$ (4×100 mL) and brine (2×100 mL). The organic portion was dried over $MgSO_4$ and concentrated to give 52.0 g of tert-butyl 2-(2-azidoethoxy)ethylcarbamate as a light brown oil.

Part D

A solution of tert-butyl 2-(2-azidoethoxy)ethylcarbamate (47.0 g, 0.204 mol) in MeOH was treated with 4 g of 10% Pd on carbon and shaken under $H_2$ (3 Kg/cm$^2$) for 24 hours. The solution was then filtered through a Celite pad and concentrated to give 35.3 g of crude tert-butyl 2-(2-aminoethoxy)ethylcarbamate as a colorless liquid that was used without further purification.

Part E

A stirred solution of 4-chloro-3-nitroquinoline (31.4 g, 0.151 mol) in 500 mL of anhydrous $CH_2Cl_2$, under $N_2$, was treated with triethylamine (43 mL, 0.308 mol) and tert-butyl 2-(2-aminoethoxy)ethylcarbamate (0.151 mol). After stirring overnight, the reaction mixture was washed with $H_2O$ (2×300 mL) and brine (300 mL). The organic portion was dried over $Na_2SO_4$ and concentrated to give a bright yellow solid. Recrystallization from ethyl acetate/hexanes gave 43.6 g of tert-butyl 2-{2-[(3-nitroquinolin-4-yl)amino]ethoxy}ethylcarbamate as bright yellow crystals.

Part F

A solution of tert-butyl 2-{2-[(3-nitroquinolin-4-yl)amino]ethoxy}ethylcarbamate (7.52 g, 20.0 mmol) in toluene was treated with 1.5 g of 5% Pt on carbon and shaken under $H_2$ (3 Kg/cm$^2$) for 24 hours. The solution was then filtered through a Celite pad and concentrated to give 6.92 g of crude tert-butyl 2-{2-[(3-aminoquinolin-4-yl)amino]ethoxy}ethylcarbamate as a yellow syrup.

Part G

A solution of tert-butyl 2-{2-[(3-aminoquinolin-4-yl)amino]ethoxy}ethylcarbamate (10.2 g, 29.5 mmol) in 250 mL of anhydrous $CH_2Cl_2$ was cooled to 0° C. and treated with triethylamine (4.18 mL, 30.0 mmol). Methoxypropionyl chloride (3.30 mL, 30.3 mmol) was then added dropwise over 5 min. The reaction was then warmed to room temperature and stirring was continued for 1 hour. The reaction mixture was then concentrated under reduced pressure to give an orange solid. This was dissolved in 250 mL of EtOH and 12.5 mL of triethylamine was added. The mixture was heated to reflux and stirred under $N_2$ overnight. The reaction was then concentrated to dryness under reduced pressure and treated with 300 mL of $Et_2O$. The mixture was then filtered and the filtrate was concentrated under reduced pressure to give a brown solid. The solid was dissolved in 200 mL of hot methanol and treated with activated charcoal. The hot solution was filtered and concentrated to give 11.1 g of tert-butyl 2-{2-[2-(2-methoxyethyl)-1H-imidazo[4,5-c]quinolin-1-yl]ethoxy}ethylcarbamate as a yellow syrup.

Part H

A solution of tert-butyl 2-{2-[2-(2-methoxyethyl)-1H-imidazo[4,5-c]quinolin-1-yl]ethoxy}ethylcarbamate (10.22 g, 24.7 mmol) in 250 mL of $CHCl_3$ was treated with 3-chloroperbenozic acid (77%, 9.12 g, 40.8 mmol). After stirring 30 minutes, the reaction mixture was washed with 1% $Na_2CO_3$ solution (2×75 mL) and brine. The organic layer was then dried over $Na_2SO_4$ and concentrated to give 10.6 g of tert-butyl 2-{2-[2-(2methoxyethyl)-5-oxido-1H-imidazo[4,5-c]quinolin-1-yl]ethoxy}ethylcarbamate as an orange foam that was used without further purification.

Part I

A solution of tert-butyl 2-{2-[2-(2-methoxyethyl)-5-oxido-1H-imidazo[4,5-c]quinolin-1-yl]ethoxy}ethylcarbamate (10.6 g, 24.6 mmol) in 100 mL of 1,2-dichloroethane was heated to 60° C. and treated with 10 mL of concentrated $NH_4OH$ solution. To the rapidly stirred solution was added solid p-toluenesulfonyl chloride (7.05 g, 37.0 mmol) over a 10 minute period. The reaction mixture was treated with an additional 1 mL concentrated $NH_4OH$ solution and then sealed in a pressure vessel and heating was continued for 2 hours. The reaction mixture was then cooled and treated with 100 mL of $CHCl_3$. The reaction mixture was then washed with $H_2O$, 1% $Na_2CO_3$ solution (2×) and brine. The organic portion was dried over $Na_2SO_4$ and concentrated to give 10.6 g of tert-butyl 2-{2-[4-amino-2-(2-methoxyethyl)-1H-imidazo[4,5-c]quinolin-1-yl]ethoxy}ethylcarbamate as a brown foam.

Part J

Tert-butyl 2-{2-[4-amino-2-(2-methoxyethyl)-1H-imidazo[4,5-c]quinolin-1-yl]ethoxy}ethylcarbamate (10.6 g, 24.6 mmol) was treated with 75 mL of 2M HCl in ethanol and the mixture was heated to reflux with stirring. After 1.5 hours, the reaction mixture was cooled and filtered to give a gummy solid. The solid was washed ethanol and $Et_2O$ and dried under vacuum to give the hydrochloride salt as a light brown solid. The free base was made by dissolving the hydrochloride salt in 50 mL of $H_2O$ and treating with 10% NaOH solution. The aqueous suspension was then concentrated to dryness and the residue was treated with $CHCl_3$. The resulting salts were removed by filtration and the filtrate was concentrated to give 3.82 g of 1-[2-(2-aminoethoxy)ethyl]-2-(2-methoxyethyl)-1H-imidazo[4,5-c]quinolin-4-amine as a tan powder.

MS 330 (M+H)$^+$;

$^1$H NMR (300 MHz, DMSO-d$_6$) δ 8.10 (d, J=8.1 Hz, 1 H); 7.66 (d, J=8.2 Hz, 1 H); 7.40 (m, 1 H); 7.25 (m, 1 H); 6.88 (br s, 2 H); 4.78 (t, J=5.4 Hz, 2 H); 3.89 (t, J=4.8 Hz, 2 H); 3.84 (t, J=6.9 Hz, 2 H); 3.54 (t, J=5.4 Hz, 2 H); 3.31 (s, 3 H); 3.23 (t, J=6.6 Hz, 2 H); 2.88 (t, J=5.3 Hz, 2 H).

Part K

Under a nitrogen atmosphere, a solution of N-hydroxysulfosuccinimidyl (azidosalicylamido)hexanoate (100 mg, 0.204 mmol of Sulfo-LC-NHS-ASA from Pierce Biotechnology, Inc, Rockford, Ill., USA) in DMF (2-4 mL) was added to a solution of 1-[2-(2-aminoethoxy)ethyl]-2-(2-methoxyethyl)-1H-imidazo[4,5-c]quinolin-4-amine (66 mg, 0.201 mmol) in DMF (5 mL). After 3.5 hours analysis by HPLC showed that no starting material was present. The reaction mixture was stirred overnight and then concentrated under reduced pressure. The residue was purified by flash chromatography (2×15 cm SiO$_2$ eluting with 8% methanol in chloroform) to provide 55 mg of product as a colorless glass. The glass was transferred using dichloromethane to a conical flask and then concentrated to provide a foam. The foam was dried overnight under high vacuum and then in a vacuum oven at 50° C. for 5 hours to provide 45 mg of product as a white fluffy solid. Analysis by HPLC indicated a purity of >95%.

IRM Compound 3 (IRM3): N-(2-{2-[4-amino-2-(2-methoxyethyl)-1H-imidazo[4,5-c]quinolin-1-yl]ethoxy}ethyl)hexadecanamide

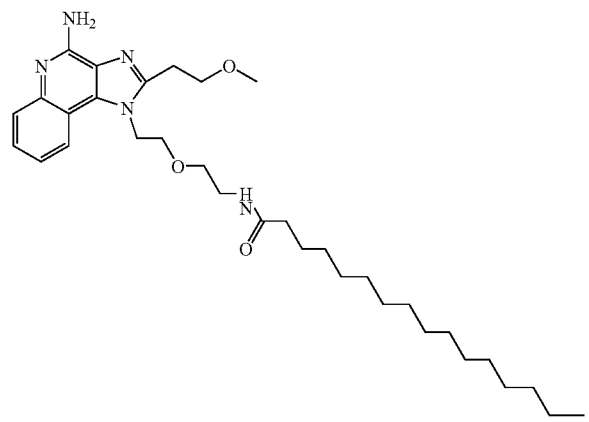

Under a nitrogen atmosphere, a suspension of 1-[2-(2-aminoethoxy)ethyl]-2-(2-methoxyethyl)-1H-imidazo[4,5-c]quinolin-4-amine (140.5 mg, 0.428 mmol) in a mixture of dichloromethane (3.5 mL) and triethylamine (150 μL, 1.07 mmol) was cooled to 0° C. Palmitoyl chloride (130 μL, 0.428 mmol) was slowly added. The reaction mixture was allowed to stir at 0° C. for 2 hours at which time analysis by thin layer chromatography indicated that there was no starting material left. The reaction mixture was diluted with dichloromethane (30 mL), washed with saturated sodium bicarbonate solution (2×5 mL), dried over magnesium sulfate and then concentrated under reduced pressure. The resulting residue was purified by column chromatography (12 g of silica gel eluted with 2% methanol in dichloromethane) to provide 183 mg of N-(2-{2-[4-amino-2-(2-methoxyethyl)-1H-imidazo[4,5-c]quinolin-1-yl]ethoxy}ethyl)hexadecanamide as a white powder.

Anal. Calcd for $C_{33}H_{53}N_5O_3$: % C, 69.80; % H, 9.41; % N, 12.33. Found: % C, 69.60; % H, 9.28; % N, 11.99.

Example 1

Crosslinking of Immune Response Modifier to Ovalbumin

IRM1 was suspended in dimethyl sulfoxide (DMSO) to 10 mg/ml. Ovalbumin was suspended in phosphate buffered saline (PBS) to 10 mg/ml and the pH adjusted to >10.0 by he addition of NaOH. 500 μl of the ovalbumin solution (5 mg ovalbumin) was mixed with 100 μl of the IRM1 solution (1 mg IRM1) in a single well of a 12-well tissue culture plate. The plate was placed on ice and a long wavelength UV light source was placed directly over the plate as close to the well containing the IRM1/ovalbumin mixture as possible. The mixture was irradiated for 15 minutes. The resulting conjugate was removed from the well and resuspended in PBS to a final concentration of 5 mg/ml ovalbumin, 0.5 mg/ml IRM1, and dialyzed against PBS to remove any unconjugated IRM.

Example 2

Immunizations

C57BL/6 mice were immunized with conjugate (1 mg ovalbumin and 200 μg IRM1, prepared as in Example 1) in 200 μl PBS either subcutaneously or intraperitoneally. Control mice were immunized with 1 mg ovalbumin in 200 μl PBS. For analysis of primary responses, mice were sacrificed 5-7 days after immunization. For analysis of secondary responses, the mice were boosted 7-15 days after the initial immunization and sacrificed 5-7 days later. Unless otherwise indicated, lymph nodes were harvested from mice immunized subcutaneously for analysis and spleen cells were harvested from mice immunized intraperitoneally for analysis.

Example 3

Reagents

Fluorochrome-labeled antibodies specific for mouse CD8, CD11c, and CD44 were obtained from Pharmingen (San Diego, Calif.). The monoclonal antibody 25D1.16 (Dr. Ron Germain, NIH) is specific for the dominant ovalbumin peptide (SIINFEKL) bound to the MHC class I molecule H-2K$^b$. Porgador et al., *Immunity* 6:715-26. Ovalbumin was obtained from Sigma Chemical Company (St. Louis, Mo.). Tetramers of the MHC class I molecule H-2K$^b$ bound to the dominant ovalbumin peptide SIINFEKL were produced as described in Kedl et al., *J Exp Med,* 192:1105-13 (2000). The ovalbumin-expressing melanoma cell line B16ova was made by lipofection of the B16-F10 cell line (ATCC # CRL-6475) with a plasmid encoding full-length ovalbumin. See Kedl et al., *Proc. Natl. Acad. Sci. USA,* 98:10811-6. Cytokine capture and detection reagents were from Miltyeni Biotech (Auburn, Calif.).

Example 4

Experimental mice were immunized with conjugate as prepared in Example 1 either subcutaneously or intraperitoneally as described in Example 2. Control mice were immunized with ovalbumin as described in Example 2. Seven days later, lymph nodes or spleen were removed and the cells were stained with antibodies specific for CD8, CD44, and H-2K$^b$/

SIINFEKL tetramers and analyzed by flow cytometry. The results are shown in FIGS. 1-3. The cells that stain positively for all three markers identify activated, ovalbumin-specific CD8$^+$ T cells that developed as a result of the immunization.

Each of FIGS. 1-3 includes the percentage of all CD8$^+$ T cells examined that were identified as activated, ovalbumin-specific CD8$^+$ T cells. In the control mice, 0.07% of CD8$^+$ T cells were activated, ovalbumin-specific CD8$^+$ T cells. Subcutaneous immunization with conjugate generated 0.52% activated, ovalbumin-specific CD8$^+$ T cells. Intraperitoneal immunization with conjugate generated 0.92% activated, ovalbumin-specific CD8$^+$ T cells.

Immunization with the dominant ovalbumin peptide (SIINFEKL) conjugated to IRM1 (100 µg peptide crosslinked to 200 µg IRM1) also induced the activation of ovalbumin-specific CD8$^+$ T cells.

Example 5

Figure 4:
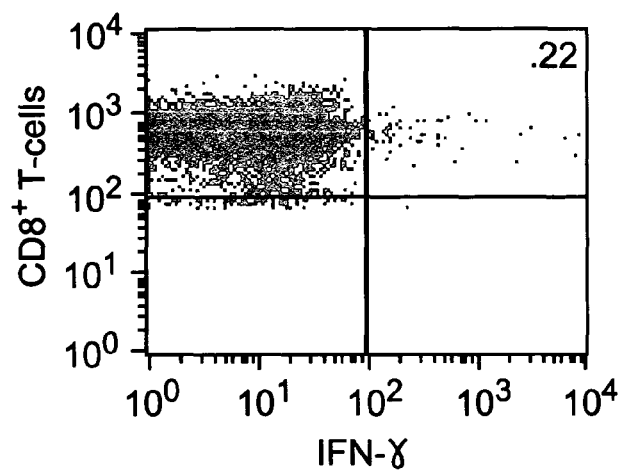
FIG. 4 shows production of interferon-γ induced by mice immunized with ovalbumin, as described in Example 5.
Figure 5:
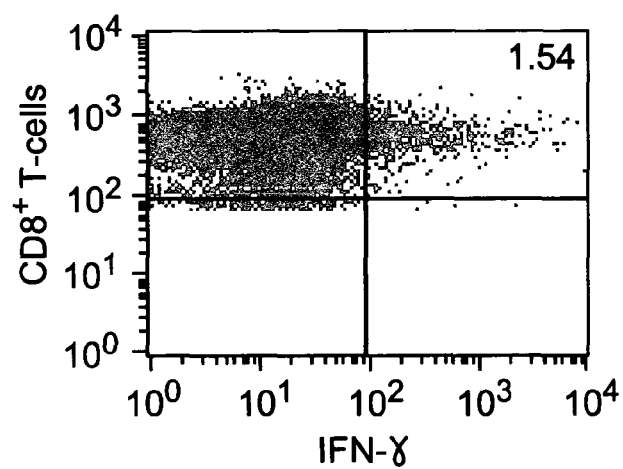
FIG. 5 shows production of interferon-γ induced by mice immunized subcutaneously with an IRM-ovalbumin conjugate, as described in Example 5.
Figure 6:
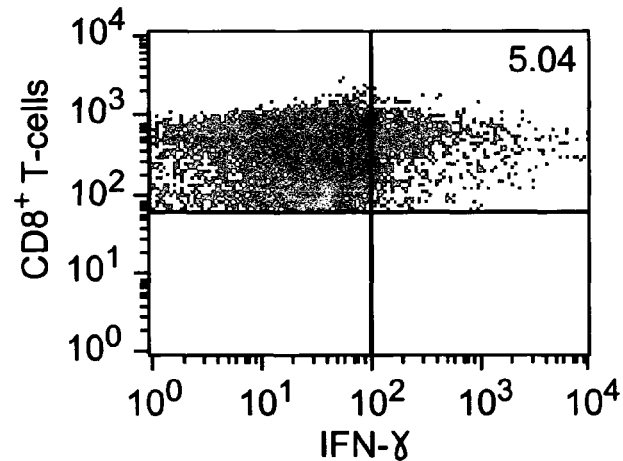
FIG. 6 shows production of interferon-γ induced by mice immunized intraperitoneally with an IRM-ovalbumin conjugate, as described in Example 5.

Control mice were immunized with ovalbumin as described in Example 2. Experimental mice were immunized with conjugate as prepared in Example 1 either subcutaneously or intraperitoneally as described in Example 2. Appropriate immune cells were harvested seven days after immunization and incubated in vitro for four hours with SIINFEKL peptide. Interferon gamma (IFN-γ)-producing CD8$^+$ T cells were identified using an IFN-γ capture and detection assay coupled with flow cytometry. CD8$^+$ T cells that were generated by immunizing with the IRM1-ovalbumin conjugate produced IFN-γ in response to subsequent antigen stimulation (FIGS. 4-6).

Example 6

Mice were immunized with conjugate as prepared in Example 1 as described in Example 2 and then boosted with an equal amount of conjugate on day 15. The spleen and lymph node cells from the boosted animals were analyzed seven days after boosting. Analysis showed an increased percentage of activated ovalbumin-specific CD8$^+$ T cells over those from mice that had received only the primary immunization (FIG. 7).

Example 7

Mice were injected intradermally with the ovalbumin-expressing melanoma cell line B16ova (1×10$^5$ cells). On day 7, the mice were injected subcutaneously with either 1 mg ovalbumin (control) or with conjugate as prepared in Example 1. On Day 14, the mice were boosted subcutaneously with ovalbumin or conjugate as on Day 7. On Day 20, tumor size was measured with calipers in two dimensions. Immunization with the conjugate resulted in reduced tumor size as compared to the control (FIG. 8).

Example 8

Figure 9:
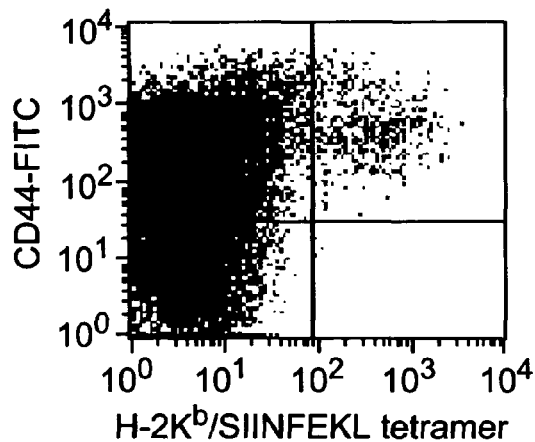
FIG. 9 shows expansion of activated tumor antigen-specific CD8+ T cells in the spleen after immunization with an IRM-tumor antigen conjugate, as described in Example 8.

Mice were injected intradermally with the ovalbumin-expressing melanoma cell line B16ova (1×10$^5$ cells). Seven and 14 days later, the mice were injected intraperitoneally with either 1 mg ovalbumin (control) or with conjugate as prepared in Example 1. Twenty days after challenge with the melanoma cell line, spleens and tumors were removed and the cells from each source were stained with antibodies specific for CD8 and CD44 as well as H-2K$^b$/SIINFEKL tetramers. Flow cytometric analysis revealed a significant expansion of activated ovalbumin-specific CD8$^+$ T cells both in the spleen (FIG. 9) and within the tumor (FIG. 10).

Example 9

Mice were immunized intravenously with ovalbumin, ovalbumin and unpaired IRM1: 1-(2-amino-2-methylpropyl)-2-(ethoxymethyl)-1H-imidazo[4,5-c]quinoline-4-amine (IRM1 prior to attachment of the linker group—the product of Part G of the synthesis of IRM1), or with conjugate as prepared in Example 1. Fourteen hours later, the spleens were removed, collagenase treated, and the cells were stained with antibodies specific for CD8, CD11c, and the antibody 25D1.16, which is specific for the ovalbumin peptide SIINFEKL complexed with the MHC class I H-2K$^b$ molecule. Flow cytometric analysis indicated that immunizing mice with the IRM1-ovalbumin conjugate (FIG. 13) generated a greater percentage of CD11c$^+$, CD8$^+$ dendritic cells that were presenting K$^b$/SIINFEKL than immunizing mice with ovalbumin alone (FIG. 11) or a mixture of unpaired ovalbumin and IRM1 (FIG. 12).

Example 10

Mice were immunized on Day 0 subcutaneously as described in Example 2 with ovalbumin (control) or with IRM1 conjugate as prepared in Example 1. The mice received boost immunizations on Day 14. The mice were then challenged intradermally with the ovalbumin-expressing melanoma cell line B16ova (1×10$^5$ cells) on Day 28 and monitored for tumor growth. At Day 75, 80% of the mice immunized with conjugate survived and appeared healthy, while all of the mice immunized with only ovalbumin died (FIG. 14).

Example 11

A stock solution of IRM3 was prepared by dissolving IRM3 in DMSO to a concentration of 10 mg/ml. Ovalbumin was dissolved in PBS to a concentration of 50 mg/ml. 50 µl of the IRM3 stock solution was added to 150 µl of PBS and then mixed by vortexing. 50 µl of the ovalbumin was added to the IRM3 solution and mixed by vortexing. A cloudy colloidal suspension of IRM3 and ovalbumin resulted.

Mice were immunized on Day 0 subcutaneously as described in Example 2 with either (a) ovalbumin alone, or (b) 50 µl of the colloidal suspension of ovalbumin and IRM3. On Day 6, draining lymph nodes were removed, homogenized, and stained with the H-2K$^b$/SIINFEKL tetramer to identify ovalbumin-specific T cells. FIG. 15 shows flow cytometry data from a control mouse immunized with ovalbumin alone; FIGS. 16 and 17 show data from two different mice that were immunized with the colloidal suspension.

Example 12

A conjugate of IRM2 and ovalbumin was prepared as described in Example 1, except that IRM2 was used in place of IRM1.

Figure 18:
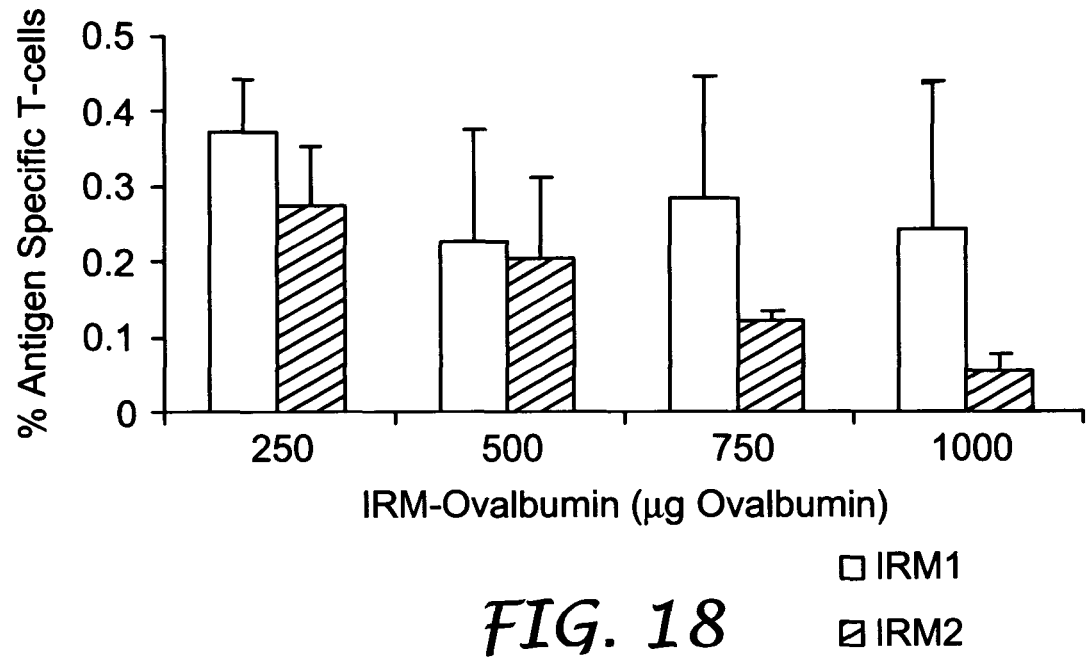
FIG. 18 shows the expansion of antigen-specific CD8+ T cells as a result of immunization with IRM-antigen conjugates using two different IRMs.

Twenty-four mice were divided into eight groups of three. Four groups of three mice were immunized subcutaneously as described in Example 2 at Day 0, with each group receiving increasing amounts of IRM1-ovalbumin conjugate. The remaining four groups were similarly immunized at Day 0 with the IRM2-ovalbumin conjugate. At day 6, the mice were sacrificed and draining lymph nodes were removed and stained with the H-2K$^b$/SIINFEKL tetramer to identify ovalbumin-specific T cells. The percentage of ovalbumin-specific T cells was calculated for each mouse. FIG. 18 summarizes the results.

Example 13

Figure 19:
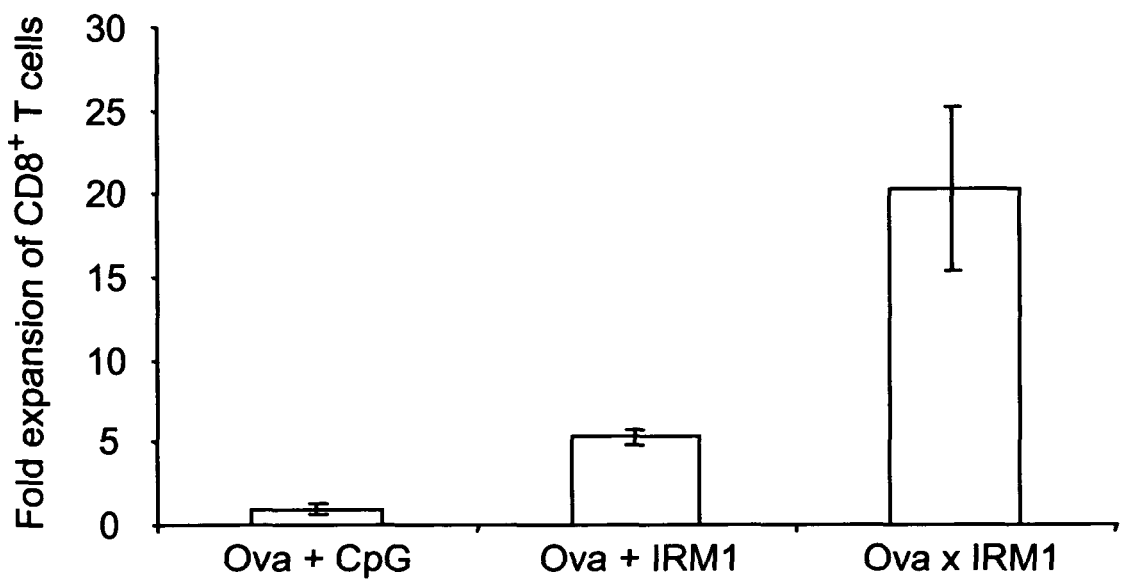
FIG. 19 shows the fold expansion of CD8+ T cells over immunization with ovalbumin alone of mice immunized with various immunostimulatory compositions.

Mice were adoptively transferred with approximately $2 \times 10^6$ OT1 ovalbumin-specific transgenic T cells (The Jackson Laboratory, Bar Harbor, Me.). Mice were immunized on Day 0 subcutaneously as described in Example 2 with either (a) 100 µg ovalbumin, (b) 100 µg ovalbumin+50 µg CpG (Ova+CpG), (c) 100 µg ovalbumin+50 µg unpaired IRM1 (Ova+IRM), or (d) 100 µg ovalbumin conjugated to 50 µg IRM1 (Ova×IRM). On Day 5, draining lymph nods were removed and the cells were stained with the H-2K$^b$/SIIN-FEKL tetramer to identify ovalbumin-specific T cells. FIG. 19 shows the fold expansion of ovalbumin-specific T cells in the Ova+CpG, Ova+IRM, and Ova×IRM groups over the mice immunized with ovalbumin alone.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

a portion having antigenic activity that comprises:
  an antigenic portion, or
  a solid support to which an antigenic moiety is paired;
wherein the immune response modifier portion is covalently coupled to the portion having antigenic activity through $R_1$, $R_2$, $R_3$, or $R_4$:
wherein the immune response modifier portion comprises an imidazoquinoline amine; a tetrahydroimidazoquinoline amine; an imidazopyridine amine; an aryl ether-substituted imidazopyridine amine; a 1,2-bridged imidazoquinoline amine; a 6,7-fused cycloalkylimidazopyridine amine; an imidazonaphthyridine amine; a tetrahydroimidazonaphihyndine amine; an oxazoloquinoline amine; a thiazoloquinoline amine; an oxazolopyridine amine; a thiazolopyridine amine; an oxazolonaphthyridine amine; or a thiazolonaphthyridine amine; and
wherein the antigenic portion or antigenic moiety comprises a polypeptide, a polynucleotide, or a lipopolysaccharide.

2. The immunostimulatory composition of claim 1 wherein the immune response modifier portion is an agonist of Toll-like receptor 2, Toll-like receptor 4, Toll-like receptor 6, Toll-like receptor 7, or Toll-like receptor 8.

3. The immunostimulatory composition of claim 1 wherein the polypeptide is a protein.

4. The immunostimulatory composition of claim 1 wherein the immune response modifier portion is a compound of the formula:

What is claimed is:

1. An immunostimulatory composition comprising:
  an immune response modifier (IRM) portion of the formula:

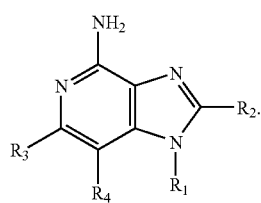

and having IRM activity; and

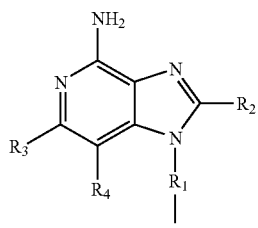

wherein:
  $R_1$ is a linker group;
  $R_2$ is selected from the group consisting of:
    -hydrogen;
    -alkyl;
    -alkenyl;

-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from the group consisting of:
  —OH;
  -halogen;
  —$N(R_5)_2$;
  —CO—$N(R_5)_2$;
  —CS—$N(R_5)_2$;
  —$SO_2$—$N(R_5)_2$;
  —$NR_5$—CO—$C_{1-10}$alkyl;
  —$NR_5$—CS—$C_{1-10}$alkyl;
  —$NR_5$—$SO_2$—$C_{1-10}$alkyl;
  —CO—$C_{1-10}$alkyl;
  —CO—O—$C_{1-10}$alkyl;
  —$N_3$;
  -aryl;
  -substituted aryl;
  -heteroaryl;
  -substituted heteroaryl;
  -heterocyclyl;
  -substituted heterocyclyl;
  —CO-aryl;
  —CO-(substituted aryl);
  —CO-heteroaryl; and
  —CO-(substituted heteroaryl);

$R_3$ and $R_4$ are each independently:
  -hydrogen;
  -halogen;
  -alkyl;
  -alkenyl;
  —O-alkyl;
  —S-alkyl; and
  —$N(R_5)_2$;
  or when taken together, $R_3$ and $R_4$ form a fused aryl or heteroaryl group that is optionally substituted by one or more substituents selected from the group consisting of;
  -halogen;
  -alkyl;
  -alkenyl;
  —O-alkyl;
  —S-alkyl; and
  —$(R_5)_2$;
  or when taken together, $R_3$ and $R_4$ form a fused 5 to 7 membered saturated ring, optionally containing one or more heteroatoms and optionally substituted by one or more substituents selected from the group consisting of;
  -halogen;
  -alkyl;
  -alkenyl;
  —O-alkyl;
  —S-alkyl; and
  —$N(R_5)_2$; and
each $R_5$ is independently hydrogen or $C_{1-10}$alkyl.

5. The immunostimalatory composition of claim 1 wherein the immune response modifier portion is covalently coupled to the portion having antigenic activity through $R_1$.

* * * * *

UNITED STATES PATENT AND TRADEMARK OFFICE
CERTIFICATE OF CORRECTION

PATENT NO. : 7,427,629 B2  Page 1 of 2
APPLICATION NO. : 10/640904
DATED : September 23, 2008
INVENTOR(S) : Ross M. Kedl It is certified that error appears in the above-identified patent and that said Letters Patent is hereby corrected as shown below:

Title Page, Item (56) Page 2
"Other Publications", delete "Cathepson" and insert -- Cathepsin --, therefor.

Column 3
Line 50, delete "desribed" and insert -- described --, therefor.

Column 6
Line 3, delete "B." and insert -- B, --, therefor.

Column 8
Line 11, delete "III" and insert -- II --, therefor.

Column 9
Line 53, delete "arylcarbonylaamino," and insert -- arylcarbonylamino, --, therefor.

Column 13
Line 16, delete "aniinoquinolin" and insert -- aminoquinolin --, therefor.
Line 29, delete "(ethoxymethy)" and insert -- (ethoxymethyl) --, therefor.
Line 33, delete "(ethoxymethy)" and insert -- (ethoxymethyl) --, therefor.

Column 14
Line 10-15, delete "$^1$H NMR (300 MHz ...........(s,6H);" and insert the same on Line 11, as a new paragraph.

Column 15
Line 35, delete "N-dimethylformaniide" and insert -- N-dimethylformamide --, therefor.

Column 16
Line 35, delete "(2methoxyethyl)" and insert -- (2-methoxyethyl) --, therefor.

Column 18
Line 11, delete "he" and insert -- the --, therefor.

UNITED STATES PATENT AND TRADEMARK OFFICE
CERTIFICATE OF CORRECTION

PATENT NO. : 7,427,629 B2
APPLICATION NO. : 10/640904
DATED : September 23, 2008
INVENTOR(S) : Ross M. Kedl It is certified that error appears in the above-identified patent and that said Letters Patent is hereby corrected as shown below:

Column 21
Line 61, in claim 1, delete "–$R_2$." and insert -- –$R_2$ --, therefor.

Column 22
Line 14, in claim 1, delete "tetrahydroimidazonaphihyndine" and insert -- tetrahydroimidazonaphthyridine --, therefor.

Column 24
Line 18, in claim 4, delete "-$(R_5)_2$;" and insert -- -$N(R_5)_2$; --, therefor.
Line 31, in claim 5, delete "immunostimalatory" and insert -- immunostimulatory --, therefor.

Signed and Sealed this

Ninth Day of June, 2009

JOHN DOLL
*Acting Director of the United States Patent and Trademark Office*